United States Patent [19]
Ferrell et al.

[11] 3,957,875
[45] May 18, 1976

[54] SYNTHESIS OF BIS[2-(N,N-DIMETHYLAMINO)ETHYL] ETHER

[75] Inventors: John Lee Ferrell, Hurricane; Fedor Poppelsdorf, Charleston, both of W. Va.

[73] Assignee: Union Carbide Corporation, New York, N.Y.

[22] Filed: June 10, 1974

[21] Appl. No.: 477,810

[52] U.S. Cl. ............................................ 260/585 B
[51] Int. Cl.² ........................................ C07C 85/06
[58] Field of Search ................. 260/585 B, 584 R

[56] References Cited
UNITED STATES PATENTS

| | | | |
|---|---|---|---|
| 2,073,671 | 3/1937 | Andrews | 260/585 B |
| 2,412,209 | 12/1946 | Dickey et al. | 260/585 B |

*Primary Examiner*—D. Horwitz
*Attorney, Agent, or Firm*—Charles J. Metz

[57] ABSTRACT

A process is disclosed which comprises reacting trimethylamine with 2-[2-(N,N-dimethylamino)ethoxy]ethanol in the presence of nickel catalyst to produce bis[2-(N,N-dimethylamino)ethyl] ether.

16 Claims, No Drawings

SYNTHESIS OF BIS[2-(N,N-DIMETHYLAMINO)ETHYL] ETHER

The invention relates to a new and valuable synthesis for bis[2-(N,N-dimethylamino)ethyl] ether, which, for brevity, will be referred to herein as "BDMEE".

BDMEE is a valuable catalyst in the urethane polymer industry, particularly in the production of flexible urethane foams. In this connection, see, for instance, Poppelsdorf, U.S. Pat. No. 3,330,782. Heretofore, DBMEE has been produced commercially by processes that utilize as a reactant di(2-chloroethyl) ether. Such processes are disclosed, for instance, in Poppelsdorf, U.S. Pat. Nos. 3,400,157 and 3,480,675, and in Warner, U.S. Pat. No. 3,426,072. One disadvantage inherent in the use of di(2-chloroethyl) ether is the need to employ comparatively expensive corrosion resistant equipment because of the presence of chlorides. Also, the chloride by-products must be disposed of in a way that does not cause undue harm to the environment.

The present invention is based upon the discovery of a new and valuable process for producing BDMEE that does not require the use of halides, thereby eliminating the disadvantages enumerated above. The process of the invention comprises reacting trimethylamine with 2-[2-(N,N-dimethylamino)ethoxy]ethanol ("DMEE") in the presence of nickel catalyst, for a period of time and at a temperature sufficient to produce bis[2-(N,N-dimethylamino)ethyl] ether.

The following reaction summarizes the overall desired chemical transformation that occurs in the process of the invention.

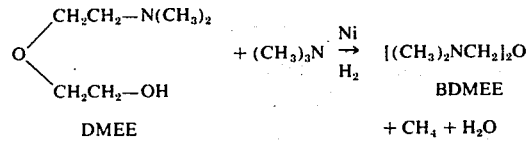

The DMEE reactant is a known composition that can be produced by reacting two moles of ethylene oxide with one mole of dimethylamine, or by adding one mole of ethylene oxide to N,N-dimethylethanolamine.

The process of the invention is preferably carried out as a batch process in the liquid phase, although it can also be carried out continuously in the liquid phase. A convenient way to carry out the process is to introduce the reactants and catalyst, along with an inert diluent, if desired, into a reaction vessel equipped with heat transfer means, agitator, and other conventional means for controlling chemical reactions, and which is capable of withstanding the autogenous pressure developed by the process. At the preferred conditions for the process, which are set forth below, the autogenous pressure is about 800 to 900 p.s.i.g. No major advantage has been obtained by using inert diluents, although dioxane, tetrahydrofuran, and methanol have been tried. Tetrahydrofuran improved the yield slightly, dioxane appeared to have no effect, and methanol had an inhibiting effect on the desired reaction and increased the production of by-product methane.

The proportions of the reactants are not narrowly critical. The desired reaction will occur at virtually any reasonable proportion of reactants, but as a practical matter, at least one mole of trimethylamine per mole of DMEE should be employed. The preferred proportions are from 2 to 3 moles of trimethylamine per mole of DMEE. Much higher proportions of trimethylamine could also be used (and, in fact, will improve the efficiency of the reaction), but economic factors and the ability of the reaction vessel to contain the pressure of large proportions of trimethylamine combine to make such higher proportions not preferred. At molar proportions below 1:1 (trimethylamine:DMEE), the efficiency of the reaction tends to become low, at least in part because the incidence of side reactions increases.

The catalyst employed is metallic nickel, such as Raney nickel or nickel deposited on an inert catalyst support. The catalyst is employed in catalytically effective amounts, such as, for example, from 0.2 to 30 weight percent, based on weight of reactants. The preferred proportion is from 0.5 to 1.5 weight percent of Raney nickel, based upon weight of reactants. These proportions are based upon the assumption of using a batch process.

It is preferred to carry out the reaction under an inert atmosphere, such as nitrogen. Hydrogen has also been employed as the atmosphere, but the efficiency of the reaction is better under nitrogen.

The process is carried out at an elevated temperature and for a period of time sufficient to produce the desired BDMEE product. Broadly, temperatures within the range of about 50° to about 300°C. are operative, with temperatures between about 180° and 190°, being preferred. Reaction times (for a batch process) can vary from about 5 to about 100 hours, and preferably from about 10 to about 15 hours.

The preferred proportions, temperature, and time set forth above, give the best compromise between productivity (i.e., percent conversion of reactants) and efficiency (i.e., lowest incidence of undesired side reactions). The major side reactions include the production of N-methylmorpholine, and higher boiling residues which have not been completely identified.

The BDMEE can be recovered by conventional techniques. For instance, the reaction mixture can be filtered to remove catalyst, and then fractionally distilled, first under pressure to recover unreacted trimethylamine (b.p. 34°C. at 30 p.s.i.g.), then at atmospheric pressure to remove water/N-methylmorpholine azeotrope, and then at reduced pressure to recover the product BDMEE (b.p. 101°C. at 40 millimeters of mercury pressure) and unreacted DMEE (b.p. 118°C. at 40 mm.). The product may contain a small amount of incompletely methylated amine (such as

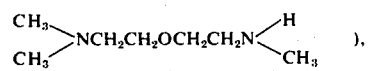

which can be removed by treating the product with acetic anhydride, followed by redistillation.

The following Table displays typical reaction conditions for laboratory size and commercial production size batches of the process:

TABLE I

| | SCALE OF PROCESS | |
|---|---|---|
| | Commercial | Laboratory |
| Reactor (Stainless Steel) | 7000 gallon, Spherical | 1 gallon autoclave |
| Catalyst | Raney nickel | Raney nickel |
| Catalyst Concentration, Weight Percent of Total Reactor Charge | 0.8 | 0.5 |
| DMEE, weight | 10,600 pounds | 760 grams |

TABLE I-continued

| | SCALE OF PROCESS | |
|---|---|---|
| | Commercial | Laboratory |
| Trimethylamine, weight | 14,000 pounds | (6 moles) 1060 grams (18 moles) |
| Reaction Time, hours | 14 | 36 |
| Temperature, °C. | 180 | 180 |
| Initial pressure, p.s.i.g. | — | 30 |
| Autogenous pressure, p.s.i.g. | about 800 | 820 |
| Yield, percent | 24 | 29.5 |
| Efficiency | 32 | 33.4 |

The Examples which follow illustrate the invention, and also illustrate attempts to produce BDMEE by processes that are analogous to certain prior art syntheses of amines. All parts are by weight, unless otherwise stated.

EXAMPLE 1

Synthesis of Bis[2-N,N-Dimethylamino)ethyl] ether Using Large Trimethylamine Excess To a gallon, stainless steel, stirred autoclave were charged 198 grams of 2-[2-(N,N-dimethylamino)-ethoxy]ethanol (DMEE) (1.5 moles), previously prepared by the addition of two moles of ethylene oxide to one mole of dimethylamine, 1330 grams of trimethylamine (22.5 moles), and 37 grams of Raney nickel catalyst wet with an equal weight of water. This mixture was heated under nitrogen to 170°C., with stirring, and allowed to remain at this temperature 32 hours, at which point gas chromatographic analysis of the reactor material indicated that over 90% of the DMEE had been converted. The reactor was then cooled to 20°C. and the reaction mixture was forced out of the autoclave into a dry ice-cooled cold trap. After filtration and removal of excess trimethylamine, distillation of the mixture on a spinning band column afforded 96 grams (40% yield) of BDMEE (b.p. 100–101°C./40 mm.).

EXAMPLE 2

Synthesis of Bis[2-(N,N-Dimethylamino)ethyl] ether Using Moderate Trimethylamine Excess To the same one-gallon autoclave described in Example 1 was charged 790 grams of DMEE (6 moles), 1060 grams of trimethylamine (18 moles), and 10 grams of Raney nickel. This mixture was heated to 180°C. as in Example 1 and allowed to remain at this temperature for 36 hours. Distillation of the reaction mixture on a 35-tray Oldershaw column afforded 285 grams (29% yield) of BDMEE.

EXAMPLE 3

Bis[2-(N,N-Dimethylamino)ethyl] Ether Synthesis at 200°C.

To a 1000 cc, stainless steel, stirred autoclave was charged 132 grams of DMEE (1 mole), 295 grams of trimethylamine (5 moles), and 4 grams of Raney nickel. The mixture was heated under nitrogen to 200°C. with stirring and allowed to remain at this temperature for 17 hours. At this point, gas chromatographic analysis of the reactor material showed the DMEE to be almost completely converted and the mixture to contain about 33 grams of BDMEE ( ~ 21% yield). The reactor product was not distilled.

EXAMPLE 4

BDMEE Synthesis Using a Harshaw Nickel Catalyst

To the same 1000 cc autoclave described in Example 3 was charged 158 grams of DMEE (1.2 moles), 185 grams of trimethylamine (3.1 moles), and 30 grams of Harshaw Ni-1404P catalyst[1]. The mixture was placed under 100 p.s.i.g. of hydrogen and heated to 155°C. with stirring. After 18 hours at 155°C., gas chromatographic analysis of the reactor material indicated that a BDMEE yield of 40% was reached at 85% DMEE conversion. Subsequent analysis after 22, 28, and 39 hours gave evidence of BDMEE destruction with concomitant production of N-methylmorpholine and high molecular weight by-products. After 39 hours at 155°C. the BDMEE yield had dropped off to 23% at 99% DMEE conversion.

[1] 70 Weight percent nickel impregnated in an alumina support.

EXAMPLE 5

BDMEE Synthesis from DMEE and Dimethylamine

To a 1000 cc. stirred autoclave was charged 100 grams of DMEE (0.76 mole), 170 grams of dimethylamine (3.8 moles), and 8 grams Raney nickel. The mixture was placed under a nitrogen atmosphere and heated to 190°C. with stirring. After 36 hours at 190°C., gas chromatographic analysis of the reactor product indicated that a BDMEE yield of about 8% had been reached at about 65% DMEEE conversion. Subsequent analyses showed that DMEE was being converted to other products at a faster rate than to BDMEE so the reaction was stopped after 48 hours. The reactor product was not distilled.

EXAMPLE 6

Attempted Synthesis of BDMEE Using Raney Cobalt Catalyst

To a 1000 cc. stirred autoclave was charged 132 grams of DMEE (1 mole), 177 grams of trimethylamine, and 20 grams of Raney cobalt. The mixture was placed under nitrogen and heated at 200°C., 225°C., and 250°C. There was no evidence of reaction after 48 hours up to 225°C. At 250°C., gas chromatographic analysis indicated a slow rate of DMEE conversion to N-methylmorpholine. Only a trace of BDMEE was produced at these reaction conditions. The reaction was repeated under a hydrogen atmosphere with no better results.

EXAMPLE 7

Attempted BDMEE Synthesis Using Copper Chromite Catalysts

Reaction conditions of Example 6 were repeated in two separate reactions employing 20 grams portions Harshaw copper chrome catalysts C-0203 and Cu-1407, respectively. In each case, no appreciable reaction occurred under 200°C. with N-methylmorpholine being the major reaction product above 200°C. Only traces of BDMEE were produced in each case.

Example 5 illustrates that the reaction of the alcohol (DMEE) with dimethylamine is unsatisfactory for the synthesis of BDMEE. Example 6 illustrates the selectivity of the nickel-containing catalyst by pointing out that not just any hydrogenation catalyst will work in the synthesis of BDMEE.

Example 7 illustrates that the method of Toshio Agawa et al., Yukagaku 14 (10), 556-9 (1965) (Japan), is unsatisfactory for the synthesis of BDMEE.

What is claimed is:

1. Process for producing bis[2-(N,N-dimethylamino)ethyl] ether which comprises reacting trimethylamine with 2-~2-(N,N-dimethylamino)ethoxy]ethanol in the liquid phase, in the presence of a catalytically effective amount of metallic nickel catalyst, for a period of time and at a temperature sufficient to produce bis[2-(N,N-dimethylamino)ethyl] ether, said temperature being within the range of from 50°C. to 300°C.

2. Process of claim 1 wherein the time is within the range of 5 to 100 hours.

3. Process of claim 1 wherein the temperature is within the range of from about 180° to about 190°C.

4. Process of claim 3 wherein the time is within the range of from about 10 to about 15 hours.

5. Process of claim 1 wherein the catalyst is Raney nickel.

6. Process of claim 2 wherein the catalyst is Raney nickel.

7. Process of claim 1 wherein the molar proportion of trimethylamine to 2-[2-(N,N-dimethylamino)ethoxy]ethanol is at least 1:1.

8. Process of claim 2 wherein the molar proportion of trimethylamine to 2-[2-)N,N-dimethylamino)ethoxy]ethanol is at least 1:1.

9. Process of claim 3 wherein the molar proportion of trimethylamine to 2-[2-(N,N-dimethylamino)ethoxy]ethanol is at least 1:1.

10. Process of claim 5 wherein the molar proportion of trimethylamine to 2-[2-(N,N-dimethylamino)ethoxy]ethanol is at least 1:1.

11. Process of claim 1 wherein i the molar proportion of trimethylamine to 2-[2-(N,N-dimethylamino)ethoxy]ethanol 2-(N,N-dimethylaminolethoxy]within the range of from about 2:1 to about 3:1.

12. Process of claim 2 wherein the molar proportion of trimethylamine to 2-[2-(N,N-dimethylamino)ethoxy]ethanol is within the range of from about 2:1 to about 3:1.

13. Process of claim 3 wherein the molar proportion of trimethylamine to 2-[2-(N,N-dimethylamino)ethoxy]ethanol is within the range of from bout 2:1 to about 3:1.

14. Process of claim 4 wherein the molar proportion of trimethylamine to 2-[2-(N,N-dimethylaminoethoxy]ethanol is within the range of from about 2:1 to about 3:1.

15. Process of claim 5 wherein the molar proportions of trimethylamine to 22-(N,N-dimethylamino)ethoxy]ethanol is within the range of from about 2:1 to about 3:1.

16. Process of claim 6 wherein the molar proportions of trimethylamine to 2-[-(N,N-dimethylamino)ethoxy]ethanol is within the range of from about 2:1 to about 3:1.

* * * * *

UNITED STATES PATENT OFFICE
CERTIFICATE OF CORRECTION

Patent No. 3,957,875                     Dated May 18, 1976

Inventor(s) J.L. Ferrell and F. Poppelsdorf

It is certified that error appears in the above-identified patent and that said Letters Patent are hereby corrected as shown below:

Col. 1, line 12, "DBMEE" should read --BDMEE--.

Col. 1, line 37, "[(CH$_3$)$_2$NCH$_2$]$_2$O" should read

--[(CH$_3$)$_2$NCH$_2$CH$_2$]$_2$O--.

Col. 5, line 7, "2,~2-(N,N-dimethylamino) ethoxy]" should read

--2-[2-(N,N-dimethylamino)ethoxy]- --.

Col. 5, next-to-last line, "2-[2-)N,N-..." should read

--2-[2(N,N-...--.

Col. 6, line 7, delete "i" between "wherein" and "the".

Col. 6, line 9, delete "2-(N,N-dimethylaminolethoxy]" and insert therefor --is--.

Col. 6, line 17, "bout" should read --about--.

Col. 6, line 24, "22" should read --2-[2--

Col. 6, line 25, "y[" should read -- y] --

Col. 6, line 28, "2-[-" should read --2-[2- --.

Signed and Sealed this

Eighth Day of March 1977

[SEAL]

Attest:

RUTH C. MASON
Attesting Officer

C. MARSHALL DANN
Commissioner of Patents and Trademarks